US011884982B2

(12) United States Patent
Liu et al.

(10) Patent No.: US 11,884,982 B2
(45) Date of Patent: Jan. 30, 2024

(54) TUMOR MARKER, METHYLATION DETECTION REAGENT, KIT AND USE THEREOF

(71) Applicant: CREATIVE BIOSCIENCES (GUANGZHOU) CO., LTD., Guangdong (CN)

(72) Inventors: Xianglin Liu, Guangzhou (CN); Rongsong Zhao, Guangzhou (CN); Hongzhi Zou, Guangzhou (CN)

(73) Assignee: CREATIVE BIOSCIENCES (GUANGZHOU) CO., Guangdong (CN)

( * ) Notice: Subject to any disclaimer, the term of this patent is extended or adjusted under 35 U.S.C. 154(b) by 0 days.

(21) Appl. No.: 17/057,410

(22) PCT Filed: May 5, 2019

(86) PCT No.: PCT/CN2019/085583
§ 371 (c)(1),
(2) Date: Nov. 20, 2020

(87) PCT Pub. No.: WO2019/223516
PCT Pub. Date: Nov. 28, 2019

(65) Prior Publication Data
US 2021/0207222 A1 Jul. 8, 2021

(30) Foreign Application Priority Data
May 22, 2018 (CN) .......................... 201810494478.2

(51) Int. Cl.
*C12Q 1/6886* (2018.01)
*C12Q 1/6806* (2018.01)

(52) U.S. Cl.
CPC ......... *C12Q 1/6886* (2013.01); *C12Q 1/6806* (2013.01); *C12Q 2600/154* (2013.01)

(58) Field of Classification Search
None
See application file for complete search history.

(56) References Cited

U.S. PATENT DOCUMENTS

| | | | | |
|---|---|---|---|---|
| 6,773,882 B2 * | 8/2004 | Hogan | .............. | C12Q 1/6895 435/6.15 |
| 2004/0234960 A1 * | 11/2004 | Olek | .............. | C12Q 1/6827 435/6.12 |
| 2007/0042382 A1 * | 2/2007 | Cargill | .............. | C12Q 1/6883 536/23.2 |
| 2011/0098189 A1 | 4/2011 | Lapointe et al. | | |
| 2011/0229876 A1 | 9/2011 | Duerksen-Hughes et al. | | |
| 2013/0084286 A1 | 4/2013 | Januario et al. | | |
| 2013/0338020 A1 | 12/2013 | Ross et al. | | |
| 2014/0274748 A1 | 9/2014 | Ahlquist et al. | | |
| 2019/0010557 A1 | 1/2019 | Zou et al. | | |
| 2020/0149116 A1 | 5/2020 | Liu et al. | | |

FOREIGN PATENT DOCUMENTS

| | | |
|---|---|---|
| CN | 102099485 A | 6/2011 |
| CN | 103314114 A | 9/2013 |
| CN | 105543354 A | 5/2016 |
| CN | 106947822 A | 7/2017 |
| CN | 107326065 A | 11/2017 |
| CN | 107727865 A | 2/2018 |
| JP | 2008-118915 A | 5/2008 |
| JP | 2012-149994 A | 8/2012 |
| JP | 2013-545437 A | 12/2013 |
| RU | 2614254 C2 | 3/2017 |
| WO | 2009/052567 A | 4/2009 |
| WO | 2012/034170 A1 | 3/2012 |

OTHER PUBLICATIONS

Roux et al (PCR Methods and Applications (1995) vol. 4, pp. s185-s194) (Year: 1995).*
Diffenbach (PCR methods and Applications (1993) vol. 3, pp. S30-S37) (Year: 1993).*
Second Office Action dated Jan. 8, 2021 from the China National Intellectual Property Administration in CN Application No. 201810494478.2.
Second (Non-Final) Office Action dated Apr. 9, 2021 from the Taiwanese Intellectual Property Office in TW Application No. 108117743.
First (Non-Final) Office Action dated Nov. 19, 2021 from the Japanese Patent Office in JP Application No. 2020-565478.
First Office Action dated Nov. 9, 2021 from the Canadian Intellectual Property Office in CA Application No. 3100912.
First Office Action dated Aug. 11, 2021 from the Russian Intellectual Property Office in RU Application No. 2020142204.
Second Office Action dated Dec. 15, 2021 from the Russian Intellectual Property Office in RU Application No. 2020142204.
Extended European Search Report dated Mar. 10, 2022 from the European Patent Office in EP Application No. 19806465.1.
International Search Report of corresponding PCT application (PCT/CN2019/085583) and WIPO translation thereof, dated Aug. 9, 2019.
Written Opinion of International Searching Authority of corresponding PCT application (PCT/CN2019/085583), dated Aug. 9, 2019.
First Office Action, dated May 28, 2020, issued by the China National Intellectual Property Administration in corresponding Chinese Patent Application No. 201810494478.2.

(Continued)

*Primary Examiner* — Katherine D Salmon
(74) *Attorney, Agent, or Firm* — Sughrue Mion, PLLC

(57) ABSTRACT

The present invention relates to the technical field of biology. Disclosed are a tumor marker, a methylation detection reagent, a kit and application thereof. Disclosed in the present invention is that: a colorectal cancer specimen can be distinguished from a fecal specimen of a normal person by detection a methylation level of COL4A1 gene promoter region. The present invention relates to detecting colorectal cancer by using the methylation detection reagent of the gene.

14 Claims, 2 Drawing Sheets
Specification includes a Sequence Listing.

(56) References Cited

OTHER PUBLICATIONS

First Office Action, dated Oct. 15, 2020, issued by the Taiwanese Patent Office in corresponding Taiwanese Patent Application No. 108117743.
Park L. K. et al. "Genome-Wide DNA methylation analysis identifies a metabolic memory profile in patient-derived diabetic foot ulcer fibroblasts", Epigenetics, 2014, vol. 9, Issue 10, pp. 1339-1349.
Vladimir A. Naumov et al. "Genome-scale analysis of DNA methylation in colorectal cancer using Infinium HumanMethylation450 Bead Chips", Epigenetics, 2013, vol. 8, Issue 9, pp. 921-934.
Susan M. Mitchell et al., "A panel of genes methylated with high frequency in colorectal cancer", BMC Cancer, 2014, vol. 14, Issue 54, pp. 1-15.
Ana Barat et al., "Comparative Correlation Structure of Colon Cancer Locus Specific Methylation: Characterisation of Patient Profiles and Potential Markers across 3 Array-Based Datasets", Journal of Cancer, 2015, vol. 6, Issue 9, pp. 795-811.
Examination Report, dated Jun. 22, 2022, issued by IP Australia in corresponding Australian application No. 2019274886.
First Office Action of corresponding KR application KR 10-2020-7036320, dated Dec. 24, 2022.
Second Office Action of corresponding CA application CA 3,100,912, dated Nov. 1, 2022.
First Office Action of corresponding Indonesian application No. ID P00202010118, dated Jan. 19, 2023.

* cited by examiner

TUMOR MARKER, METHYLATION DETECTION REAGENT, KIT AND USE THEREOF

CROSS-REFERENCE TO RELATED APPLICATIONS

This application is a U.S. national phase application of PCT Patent Application Serial No. PCT/CN2019/085583, filed on May 5, 2019, and claims priority to and benefit of Chinese Patent Application No. 201810494478.2, filed on May 22, 2018 in the National Intellectual Property Administration, P.R.C., which are incorporated herein by reference in their entireties.

FIELD OF THE INVENTION

The present invention relates to the technical field of biology, in particular to a tumor marker, a methylation detection reagent, a kit and use thereof.

BACKGROUND OF THE INVENTION

Colorectal cancer, also known as colon cancer, is a common malignant tumor of the digestive tract. The incidence of colorectal cancer is increasing year by year in China. In some coastal areas of China, such as Shanghai and Guangzhou, the incidence of colon cancer has leaped to second place, second to that of lung cancer. It is currently believed that the formation of intestinal cancer is the result of accumulation of genetic and epigenetic defects. Early stages of colorectal cancer usually don't have any signs or symptoms, and symptoms such as blood in the feces, abdominal pain, and diarrhea may appear in the late stage. When the symptoms appear, it is often in the late stage, which brings great pain and expensive treatment to the patients. Therefore, early detection, early diagnosis and early treatment are important measures to reduce the incidence and mortality of colorectal cancer.

Screening tests can be used for early detection of intestinal cancer and precancerous lesions and removal of the lesions, thereby preventing the occurrence of intestinal cancer. At present, the screening tests for colorectal cancer mainly include occult blood test, which has the problem of being easily affected by food or low detection rate of adenoma, and enteroscopy, which is a gold standard for diagnosis of intestinal cancer but has low compliance as a screening test. Therefore, there is an urgent need for a method for screening intestinal cancer with high accuracy and compliance.

As a new screening test for intestinal cancer, a feces DNA test has been paid more and more attention. This method (Cologuard®) was incorporated into the U.S. Colorectal Cancer Screening Guidelines in 2016. The method has the characteristics of convenience, noninvasiveness, high detection rate of intestinal cancer and precancerous adenomas and the like. In order to prepare a high-performance feces DNA test kit for detecting intestinal cancer, two main obstacles including extraction of feces DNA and selection of markers need to be overcome. On the one hand, the composition of feces is complex, there are many inhibitors to downstream reactions, and there are many bacterial DNA. To extract human target genes from such a mixture, a set of highly sensitive gene extraction and purification methods is required; on the other hand, there are many markers related to colorectal cancer, especially DNA methylation markers, because studies have shown that DNA methylation is an early event of tumor formation. However, many methylation markers perform well at cellular and tissue levels, and when used in feces, blood and other screening media, their sensitivity and specificity to intestinal cancer are significantly reduced, for example, vimentin gene has 83% sensitivity in tissues, but reduced to 46% in fecal specimens. Similarly, there are genes such as SFRP1 and SFRP2. Such markers cannot meet the needs of clinical detection of colorectal cancer. Therefore, the selection of markers with high detection sensitivity and specificity on intestinal cancer in feces is a key point of gene detection of intestinal cancer in feces, and such markers are expected to be truly used in clinical detection of intestinal cancer.

SUMMARY OF THE INVENTION

In view of this, the present invention provides a tumor marker, a capture sequence, a primer pair, a probe, a methylation detection reagent, a kit and use thereof. The sensitivity of the tumor marker to intestinal cancer in feces is close to that in tissues, even higher than that in tissues.

Another object of the present invention is to provide a marker, a capture sequence, a primer pair, a probe, a methylation detection reagent, a kit and a method for non-invasively detecting tumors.

In order to achieve the objects, the present invention provides the following technical protocals:

The present invention provides use of COL4A1 gene in the preparation of tumor markers.

In some specific embodiments of the present invention, the sequence of COL4A1 gene has at least 97.8% identity to the sequence set forth in Genebank Accession No. NC_000013.11.

In some specific embodiments of the present invention, the sequence of COL4A1 gene has at least 98.9% identity to the sequence set forth in Genebank Accession No. NC_000013.11.

In some specific embodiments of the present invention, the sequence of COL4A1 gene has at least 99.9% identity to the sequence set forth in Genebank Accession No. NC_000013.11.

In some specific embodiments of the present invention, the sequence of COL4A1 gene has 100% identity to the sequence set forth in Genebank Accession No. NC_000013.11.

In some specific embodiments of the present invention, the tumor is colorectal cancer or adenoma.

In some specific embodiments of the present invention, the specimen to be tested is tissue, body fluid or excreta.

In some specific embodiments of the present invention, the tissue is intestinal tissue.

In some specific embodiments of the present invention, the body fluid includes, but is not limited to, blood, serum, plasma, extracellular fluid, tissue fluid, lymph fluid, cerebrospinal fluid, or aqueous humor.

In some specific embodiments of the present invention, the excreta is sputum, saliva, urine, or feces.

The present invention also provides use of the methylation detection reagent of COL4A1 gene in the preparation of a tumor detection reagent or a kit.

The methylation detection reagent of COL4A1 gene can be a methylation detection reagent in the prior art; in the prior art, there are various methods for detecting methylation of a target gene, such as methylation-specific PCR (MSP), methylation-specific quantitative PCR (qMSP), methylated DNA-specific binding proteins PCR, quantitative PCR and DNA chips, methylation-sensitive restriction endonucleases, bisulfite sequencing or pyrosequencing, etc. Each detection method has its corresponding reagents, and all these reagents can be used in the present invention to detect the methylation of COL4A1 gene.

The present invention also provides a capture sequence having any one of the nucleotide sequences shown below:
I. a nucleotide sequence shown in SEQ ID NO: 1;
II. a nucleotide sequence obtained by modifying, substituting, deleting or adding one or more bases to the nucleotide sequence shown in SEQ ID NO: 1, or a functionally similar nucleotide sequence obtained from CpG islands of the nucleotide sequence shown in SEQ ID NO: 1;
III. a sequence having at least 80%, at least 85%, at least 90%, at least 95% or at least 99% identity to the nucleotide sequence shown in SEQ ID NO: 1 or a functionally similar nucleotide sequence obtained from CpG islands of the nucleotide sequence shown in SEQ ID NO: 1; and
IV. complementary sequences of the sequences shown as I, II or III.

The present invention also provides a primer pair, wherein the upstream primer has any one of the nucleotide sequences shown below:
V. a nucleotide sequence shown in SEQ ID NO: 2;
VI. a nucleotide sequence obtained by modifying, substituting, deleting or adding one or more bases to the nucleotide sequence shown in SEQ ID NO: 2;
VII. a nucleotide sequence having at least 80%, at least 85%, at least 90%, at least 95%, or at least 99% identity to the nucleotide sequence shown in SEQ ID NO: 2, or a functionally similar nucleotide sequence obtained from CpG islands of the nucleotide sequence shown in SEQ ID NO: 2; and
VIII. complementary sequences of the sequences shown in V, VI or VII;
the downstream primer has any one of the nucleotide sequences shown below:
IX. a nucleotide sequence shown in SEQ ID NO: 3;
X. a nucleotide sequence obtained by modifying, substituting, deleting or adding one or more bases to the nucleotide sequence shown in SEQ ID NO: 3;
XI. a nucleotide sequence having at least 80%, at least 85%, at least 90%, at least 95%, or at least 99% identity to the nucleotide sequence shown in SEQ ID NO: 3, or a functionally similar nucleotide sequence obtained from CpG islands of the nucleotide sequence shown in SEQ ID NO: 3; and
XII. complementary sequences of the sequences shown in IX, X or XI.

The present invention also provides a probe having any one of the nucleotide sequences shown below:
XIII. a nucleotide sequence shown in SEQ ID NO: 4;
XIV. a nucleotide sequence obtained by modifying, substituting, deleting or adding one or more bases to the nucleotide sequence shown in SEQ ID NO: 4;
XV. a sequence having at least 80%, at least 85%, at least 90%, at least 95% or at least 99% identity to the nucleotide sequence shown in SEQ ID NO: 4, or a functionally similar nucleotide sequence obtained from CpG islands of the nucleotide sequence shown in SEQ ID NO: 4; and
XVI. complementary sequences shown in XIII, XIV or XV.

The present invention also provides a methylation detection reagent of COL4A1 gene, which comprises a capture sequence, a primer and/or a probe for detection of methylation of COL4A1 gene.

In some specific embodiments of the present invention, a capture sequence, a primer and/or a probe obtained from CpG islands of COL4A1 gene are included.

In some specific embodiments of the present invention, the primer and/or probe detect methylation of COL4A1 gene by quantitative methylation-specific PCR (qMSP).

In some specific embodiments of the present invention, the methylation detection reagent provided by the present invention detects the methylation levels in genosome, an intergenic region or a promoter region and a region near the promoter region of COL4A1 gene.

The methylation that exists in tumor tissues is considered to be an apparent modification of DNA with potential clinical value. The genosome, an intergenic region, a promoter region or a region near the promoter region are all methylated, which may be related to tumors. Currently, it has been demonstrated in a variety of tumors that aberrant methylation of CpG islands at or near the tumor suppressor gene promoter leads to transcriptional inactivation.

In some specific embodiments of the present invention, the methylation detection reagent provided by the present invention includes a capture sequence, a primer and/or a probe obtained from CpG islands at or near the promoter region of COL4A1 gene.

In some specific embodiments of the present invention, the capture sequence in the methylation detection reagent provided by the present invention has any one of the nucleotide sequences shown below:
I. a nucleotide sequence shown in SEQ ID NO: 1;
II. a nucleotide sequence obtained by modifying, substituting, deleting or adding one or more bases to the nucleotide sequence shown in SEQ ID NO: 1, or a functionally similar nucleotide sequence obtained from CpG islands of the nucleotide sequence shown in SEQ ID NO: 1;
III. a sequence having at least 80%, at least 85%, at least 90%, at least 95% or at least 99% identity to the nucleotide sequence shown in SEQ ID NO: 1 or a functionally similar nucleotide sequence obtained from CpG islands of the nucleotide sequence shown in SEQ ID NO: 1; and
IV. complementary sequences of the sequences shown as I, II or III.

In some specific embodiments of the present invention, the upstream primer of the primers in the methylation detection reagent provided herein has any one of the nucleotide sequences shown below:
V. a nucleotide sequence shown in SEQ ID NO: 2;
VI. a nucleotide sequence obtained by modifying, substituting, deleting or adding one or more bases to the nucleotide sequence shown in SEQ ID NO: 2;
VII. a nucleotide sequence having at least 80%, at least 85%, at least 90%, at least 95%, or at least 99% identity to the nucleotide sequence shown in SEQ ID NO: 2, or a functionally similar nucleotide sequence obtained from CpG islands of the nucleotide sequence shown in SEQ ID NO: 2; and
VIII. complementary sequences of the sequence shown in V, VI or VII.

In some specific embodiments of the present invention, the downstream primer of the primers in the methylation detection reagent provided herein has any one of the nucleotide sequences shown below:

IX. a nucleotide sequence shown in SEQ ID NO: 3;
X. a nucleotide sequence obtained by modifying, substituting, deleting or adding one or more bases to the nucleotide sequence shown in SEQ ID NO: 3;
XI. a nucleotide sequence having at least 80%, at least 85%, at least 90%, at least 95%, or at least 99% identity to the nucleotide sequence shown in SEQ ID NO: 3, or a functionally similar nucleotide sequence obtained from CpG islands of the nucleotide sequence shown in SEQ ID NO: 3; and
XII. complementary sequences of the sequences shown in IX, X or XI.

In some specific embodiments of the present invention, the probe in the methylation detection reagent provided herein has any one of the nucleotide sequences shown below:
XIII. a nucleotide sequence shown in SEQ ID NO: 4;
XIV. a nucleotide sequence obtained by modifying, substituting, deleting or adding one or more bases to the nucleotide sequence shown in SEQ ID NO: 4;
XV. a sequence having at least 80%, at least 85%, at least 90%, at least 95% or at least 99% identity to the nucleotide sequence shown in SEQ ID NO: 4, or a functionally similar nucleotide sequence obtained from CpG islands of the nucleotide sequence shown in SEQ ID NO: 4; and
XVI. complementary sequences shown in XIII, XIV or XV.

The present invention also provides a kit for detecting tumors, which comprises a capture sequence, a primer pair, a probe or a methylation detection reagent.

In some specific embodiments of the present invention, the kit provided herein includes: one or more containers divided for receiving reagents.

In some specific embodiments of the present invention, the kit provided herein includes: a first container comprising a capture sequence; a second container comprising a primer pair for amplification; and a third container comprising a probe.

In some specific embodiments of the present invention, the kit provided herein further comprise reagents commonly used in kits, for example, conversion reagents commonly used in qMSP, for converting unmethylated cytosine bases to uracil, while methylated cytosine bases remain unchanged. The conversion agents include, but are not limited to, hydrosulphite, bisulfite or hydrazine salts, and the like; and for example, DNA polymerases, dNTPs, $Mg^{2+}$ ions and buffers commonly used in the amplification of COL4A1 gene.

The present invention also provides use of the capture sequence, the primer pair, the probe, the methylation detection reagent and the kit in detecting tumors.

The present invention also provides a tumor detection method, which is used for distinguishing a normal specimen from a tumor specimen by detecting the methylation level of COL4A1 gene.

In some specific embodiments of the present invention, the method comprises the steps of:
(1) detecting methylation level of COL4A1 gene of a subject;
(2) comparing the methylation level of COL4A1 gene of a subject with the methylation level of a normal control specimen;
(3) indicating that the subject has or is at a risk of developing a tumor, so as to distinguish a normal specimen from a tumor specimen, according to the increase in the methylation level of COL4A1 gene of the subject compared with the methylation level of the normal control specimen.

In some specific embodiments of the present invention, the present invention detects methylation levels in genosome, an intergenic region or a promoter region and a region near the promoter region of COL4A1 gene.

In some specific embodiments of the present invention, the present invention distinguishes a normal specimen from a tumor specimen by detecting methylation levels in a promoter region and a region near the promoter region of COL4A1 gene.

In some specific embodiments of the present invention, the methylation level is detected by methylation-specific PCR, or methylation-specific quantitative PCR (qMSP), or methylated DNA-specific binding proteins PCR, quantitative PCR, and DNA chips, or methylation-sensitive restriction endonucleases, or bisulfite sequencing, or pyrosequencing.

In some specific embodiments of the present invention, the methylation level is detected by methylation-specific quantitative PCR (qMSP).

In some specific embodiments of the present invention, the methylation level is detected using said capture sequence, primer pair, probe, methylation detection reagent, or said kit.

In some specific embodiments of the present invention, in step (1), detecting the methylation level of COL4A1 gene of the subject comprises the steps of:
a) extracting DNA of a specimen to be detected by adopting a magnetic bead capture method;
b) converting the DNA of the specimen to be detected by hydrosulphite, bisulfite or hydrazine salt;
c) performing detection by methylation-specific quantitative PCR (qMSP).

In some specific embodiments of the present invention, in the step a), extracting the DNA of the specimen to be detected by adopting a magnetic bead capture method comprises the following steps:
mixing and grinding a specimen to be detected in a protective liquid, followed by centrifuging, and taking supernatant;
centrifuging the supernatant, taking the supernatant, adding a lysis solution and magnetic beads with specific complementary oligonucleotide capture sequences into the supernatant for incubation;
discarding part of the supernatant, washing off the magnetic beads and transferring to a clean centrifuge tube, adding washing liquid, performing incubation under 100-2000 rpm at room temperature for 0.5-5 min, placing on a magnetic frame and pipetting the supernatant, and repeating 3 times;
and eluting the target gene DNA with a buffer.

In some specific embodiments of the present invention, the detection criteria is that a tumor specimen and a normal specimen are interpreted according to a threshold value, wherein the threshold value of the Ct value in the fecal specimen is 32-42, preferably, the threshold value of Ct value in the fecal specimen is 35.2, if the Ct value of the fecal specimen is less than the threshold value of the Ct value, it is interpreted as a tumor specimen, and if the Ct value of the fecal specimen is greater than or equal to the threshold value of the Ct value, then it is interpreted as a normal specimen; the threshold value of the methylation level value in the tissue specimen is 1-10, preferably, the threshold value of Ct value in the fecal specimen is 3.9, if the methylation level value of the tissue specimen is greater than the threshold value of the methylation level value, it is interpreted as a tumor specimen; if the methylation level value is less than or equal to the threshold value of the methylation level value, it is interpreted as a normal specimen. The threshold can be adjusted according to the actual situation.

The present invention also provides a tumor detection system, which comprises the following components:
(1) a methylation detection component of COL4A1 gene;
(2) a data processing component;
(3) a result output member;

In some specific embodiments of the present invention, the methylation detection component comprises one or more of a fluorescent quantitative PCR instrument, a PCR instrument, and a sequencer;

In some specific embodiments of the present invention, the methylation detection component further comprises a capture sequence, a primer pair, a probe, a methylation detection reagent or kit.

In some specific embodiments of the present invention, the data processing component is configured to a. receive test data of a specimen to be tested and a normal control specimen; b. store test data of a specimen to be tested and a normal control specimen; c. compare test data of a specimen to be tested of the same type and a normal control specimen; and d. respond to the probability or possibility that a subject suffers from a tumor according to the comparison results.

In some specific embodiments of the present invention, the result output component is used for outputting the probability or possibility that a subject suffers from a tumor.

In some specific embodiments of the present invention, the judgment criteria of the data processing component is as follows: interpreting a tumor specimen and a normal specimen according to a threshold value;
wherein the threshold value of the Ct value in the fecal specimen is 32-42, preferably, the threshold value of Ct value in the fecal specimen is 35.2, if the Ct value of the fecal specimen is less than the threshold value of the Ct value, it is interpreted as a tumor specimen, and if the Ct value of the fecal specimen is greater than or equal to the threshold value of the Ct value, then it is interpreted as a normal specimen; the threshold value of the methylation level value in the tissue specimen is 1-10, preferably, the threshold value of Ct value in the fecal specimen is 3.9, if the methylation level value of the tissue specimen is greater than the threshold value of the methylation level value, it is interpreted as a tumor specimen; if the methylation level value is less than or equal to the threshold value of the methylation level value, it is interpreted as a normal specimen. The threshold can be adjusted according to the actual situation.

In some specific embodiments of the present invention, the tumor of the present invention is colorectal tumor.

In some specific embodiments of the present invention, the tumor of the present invention is colorectal cancer or adenoma.

In some specific embodiments of the present invention, a specimen to be tested or specimen type provided by the present invention is tissue, body fluid, or excreta.

In some specific embodiments of the present invention, the tissue is intestinal tissue.

In some specific embodiments of the present invention, the bodily fluid comprises blood, serum, plasma, extracellular fluid, tissue fluid, lymph fluid, cerebrospinal fluid, or aqueous humor.

In some specific embodiments of the present invention, the excreta is sputum, urine, saliva, or feces.

Through research in the present invention, it is found that by detecting the methylation level of the promoter region of COL4A1 gene, colorectal cancer specimens can be distinguished from normal human fecal specimens. According to the present invention, the detection reagent containing the methylation of the gene is used for detecting colorectal cancer, with high detection sensitivity and specificity to intestinal cancer.

Compared with the existing marker for detecting intestinal cancer, the marker and the technical protocal provided by the present invention can detect colorectal cancer with high sensitivity and specificity, and the detection rate of colorectal cancer in feces is higher than that in a tissue specimen.

1. According to the above technical protocal, the methylation detection reagent of COL4A1 gene can detect 83.8% of colorectal cancer in a fecal specimen with a specificity of 95.2%, unobviously, the detection rate of the colorectal cancer in a fecal specimen is higher than that in a tissue specimen, the feces can be simply used as a detection specimen, and the colorectal cancer can be reliably diagnosed. It is very easy to obtain the fecal specimen, the sampling is non-invasive and simple, and it will not cause any pain and inconvenience to the patient.
2. According to the above technical protocal, the methylation detection reagent of COL4A1 gene can detect 81.9% of colorectal cancer in a tissue specimen with a specificity of 95.2%.
3. According to the technical protocal, the methylation detection reagent and the extraction detection method for COL4A1 gene can conveniently and accurately judge colorectal cancer and normal people, and the methylation detection reagent of the gene is expected to be used in a feces gene detection kit and serves for clinical detection of intestinal cancer.
4. According to the reagent/kit in the technical protocal, the cancer is detected and diagnosed through the methylation level, more and more researches prove that methylation change is an early event in the tumorigenesis process, and it is easy to find early lesions by detection of methylation abnormality.

BRIEF DESCRIPTION OF THE DRAWINGS

In order to more clearly illustrate the embodiments of the present invention or the prior art, the accompanying drawings, which are needed in the description of the embodiments or the prior art, will now be described briefly.

DETAILED DESCRIPTION OF THE INVENTION

Figure 1:
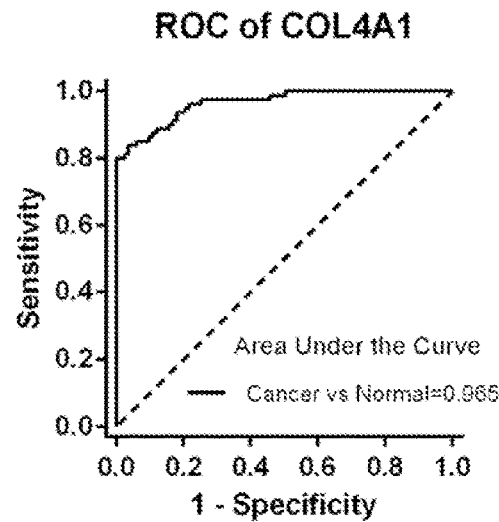
FIG. 1 shows a ROC curve of COL4A1 gene for colorectal cancer detection in the feces test of Example 1.

The present invention discloses a tumor marker, a methylation detection reagent, a kit and use thereof, and those skilled in the art can learn from the content of this article and appropriately improve the process parameters. It is specifically noted that all similar substitutes and modifications obvious to those skilled in the art are deemed to be included in the present invention. While the methods and uses of the present invention have been described in terms of preferred embodiments, it will be apparent to those skilled in the art that the techniques of the present invention may be practiced and applied with modification or appropriate alteration and combination of the methods and uses described herein without departing from the spirit and scope of the present invention.

The raw materials, auxiliary materials and reagents used in the tumor marker, methylation reagent, kit and use thereof provided by the present invention can be purchased from the market or synthesized. As long as there are CpG sites that can detect differential methylation, any nucleic acid fragment of COL4A1 gene can be used in the present invention. A CpG island is a CpG-rich region in a nucleic acid sequence. CpG islands begin upstream of the promoter and extend downstream to the transcriptional region. Methylation of CpG islands on the promoter generally inhibits gene expression. CpG islands in the promoter are part of methylation, and CpG open sea in genosome has a conservative DNA methylation target. Recent studies have revealed synergistic effects of methylation of non-promoter regions (e.g., genosome and UTR) on gene expression, and the methylation of genosome may be potential therapeutic targets in cancer.

In general, CpG islands refer to regions rich in CpG dinucleotides, usually located at or near the promoter. In the present invention, CpG islands refer not only to regions rich in CpG dinucleotides at or near the promoter, but also to hybrid methylated CpG sites, or isolated CpG sites.

Typically, the CpG-containing nucleic acid is DNA. However, the present invention is applicable, for example, to specimens comprising DNA, or DNA and RNA comprising mRNA, wherein the DNA or RNA may be single-stranded or double-stranded, or DNA-RNA hybrid strands may also be included in the specimens.

"Primer" or "probe" in the present invention refers to an oligonucleotide comprising a region complementary to a sequence of at least 6 consecutive nucleotides of a target nucleic acid molecule (e.g., a target gene). In some embodiments, the primer or probe comprises a region complementary to the sequence of at least 9, at least 10, at least 11, at least 12, at least 13, at least 14, at least 15, at least 16, at least 17, at least 18, at least 19, or at least 20 consecutive or inconsecutive block nucleotides of the target molecule. When the primer or probe comprises a region complementary to at least x consecutive nucleotides of the target molecule, the primer or probe is at least 95% complementary to at least x consecutive nucleotides of the target molecule. In some embodiments, the primer or probe is at least 96%, at least 97%, at least 98%, at least 99%, or 100% complementary to the target molecule.

The "detection" in the present invention is the same as the diagnosis, and also includes the diagnosis of the middle and late stages of colorectal tumors, and also includes colorectal tumor screening, risk assessment, prognosis, disease identification, diagnosis of disease stages and selection of therapeutic targets, in addition to the early diagnosis of colorectal tumors.

The use of the colorectal tumor marker COL4A1 makes early diagnosis of colorectal tumors possible. When it is confirmed that a gene methylated in a cancer cell is methylated in a clinically or morphologically normal-appearing cells, this indicates that the normal-appearing cells are progressing toward the cancer. Thus, colorectal cancer can be diagnosed early by methylation of the colorectal tumor-specific gene COL4A1 in normal-appearing cells.

Wherein, early diagnosis refers to the possibility of detecting cancer before metastasis, preferably before morphological changes in tissues or cells can be observed.

In addition to early diagnosis of colorectal tumors, the reagents/kits of the present invention are also desirable for colorectal tumor screening, risk assessment, prognostic diagnosis, disease identification, diagnosis of disease stages, and selection of therapeutic targets.

As an alternative embodiment for the disease stages, in the progression of colorectal tumors in different stages or periods, the diagnosis can be made by measuring the degree of methylation of COL4A1 obtained from specimens. By comparing the degree of methylation of COL4A1 gene of nucleic acids isolated from specimens at each stage of colorectal cancer to the degree of methylation of COL4A1 gene of one or more nucleic acids isolated from specimens of intestinal tissue without cell proliferative disorders, a particular stage of colorectal tumor in the specimens can be detected.

The present invention is further illustrated by the following examples:

Example 1

163 cases of fecal specimens (80 cases of colorectal cancer, 83 cases of normal, all confirmed by enteroscopy or pathology) were selected and subjected to grinding centrifugation, 100 ul of capture magnetic beads (containing the capture sequence of COL4A1 gene) were added, and the mixture was subjected to operation according to the following technical protocal:

The technical protocal was as follows:
1) fecal specimens of normal person and colorectal tumor patients with enteroscopy results were collected, 1 g of feces and 4 mL of protective solution were mixed and ground, and then centrifuged at 5000 rpm for 10 min, followed by taking the supernatant and discarding the precipitate;
2) 10 mL of supernatant was taken out for centrifugation again, 3.2 mL of supernatant was taken out, 2 mL of lysis solution and 100 ul of capture magnetic beads M1 were added, followed by incubation at 92° C. for 10 min, and then standing for 1 h at room temperature;
3) the mixture was placed on a magnetic frame, part of the supernatant was discarded, the magnetic beads was washed down, the mixture was transferred to a 2 mL centrifuge tube, 800 ul of washing solution W1 was added, followed by incubation at 1300 rpm for 1 min at room temperature, placing on the magnetic frame, pipetting the supernatant, and repeating for 3 times;
4) 55 ul of eluent was added, followed by incubation at 92° C. at 1300 rpm for 10 min, placing on a magnetic frame, and transferring 50 ul of eluent into a new EP tube within 3 min;
5) the DNA fragment from the previous step was methylated using the EZ DNA Methylation Kit (Zymo Research) and 15 ul of final eluate was used for qMSP detection.

Finally, 15 ul of Bisulfite-transformed DNA was obtained. Then qMSP was performed to detect the methylation level of COL4A2.

qMSP Reaction System: 25 ul (nuclease-free water 8.2 ul, 5×Colorless GoTaq Flexi Buffer 5 ul, $MgCl_2$ (25 mM) 5 ul, dNTPs (10 mM) 1 ul, GoTaq Hot Start polymerase 0.5 ul, Forward primer (100 uM) 0.125 ul, Reverse primer (100 uM) 0.125 ul, Probe (100 uM) 0.05 ul, DNA 5 ul). Reaction procedure: 95° C. 4 min, (95° C. 20 s, 56° C. 30 s, 72° C. 30 s)×45 Cycles, 37° C. 30 s.

And finally the copy number of the gene in the specimen was calculated according to a standard curve.

The methylation sites of COL4A1 gene are relatively constant, and are mainly located on CpG islands at or near the promoter region. One set of a capture sequence, a primer and a probe was designed for these regions and used in the methylation detection reagent of COL4A1 gene.

The capture sequence, the primer and the probe contained in the reagent are as follows:

The capture sequence of COL4A1 (SEQ ID NO: 1): 5'-CTGCCCGGCGTGCGGGGGCCGCGGCGGACAGCTAGCTCTC-3' qMSP primer pair and probe of COL4A1:
Forward Primer (SEQ ID NO:2): 5'-CGTTTGGAGTCGTCGTATTC-3'
Reverse Primer (SEQ ID NO: 3): 5'-CGACGAACAACTAACTCTCG-3'
Probe (SEQ ID NO: 4): 5'-CGTAGCGTTGGAAGTTCGGTTTTT-3'

In a feces test, the ROC curve of COL4A1 gene for colorectal cancer detection is shown in FIG. 1:

For colorectal cancer, the detection sensitivity of COL4A1 gene is 83.8% (67/80), the specificity is 95.2% (79/83), and the area under ROC curve is 0.965 (95% CI: 0.941-0.989, p<0.0001).

Figure 2:
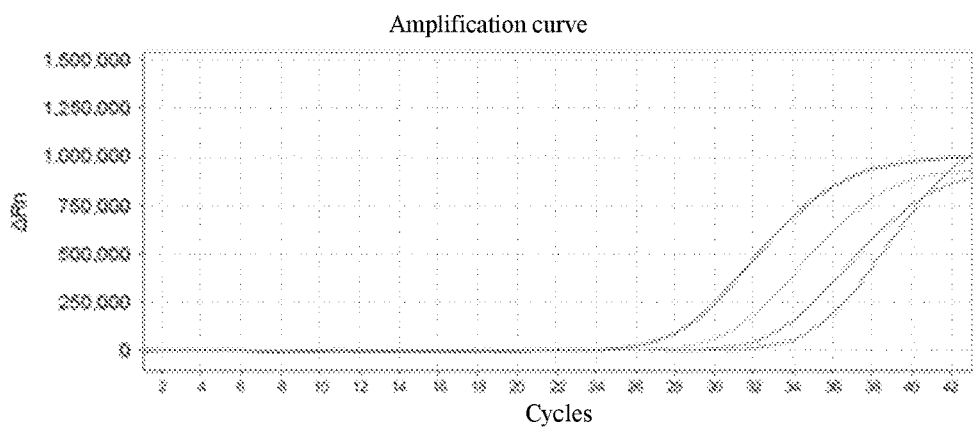
FIG. 2 shows a standard curve amplification map of COL4A1 gene in the feces test of Example 1.

In a feces test, an amplification curve of the standard curve of COL4A1 gene is shown in FIG. 2:

amplification efficiency of the standard curve is 103%, linearity $R^2=0.993$.

TABLE 1

163 cases of fecal specimens

| Classification of specimens | $C_T$ value | Detection and interpretation | Classification of specimens | $C_T$ value | Detection and interpretation |
|---|---|---|---|---|---|
| Colorectal cancer | 38 | Normal | Normal | Non-amplification | Normal |
| Colorectal cancer | 38 | Normal | Normal | Non-amplification | Normal |
| Colorectal cancer | 37 | Normal | Normal | Non-amplification | Normal |
| Colorectal cancer | 37 | Normal | Normal | Non-amplification | Normal |
| Colorectal cancer | 37 | Normal | Normal | Non-amplification | Normal |
| Colorectal cancer | 37 | Normal | Normal | Non-amplification | Normal |
| Colorectal cancer | 37 | Normal | Normal | Non-amplification | Normal |
| Colorectal cancer | 37 | Normal | Normal | Non-amplification | Normal |
| Colorectal cancer | 37 | Normal | Normal | Non-amplification | Normal |
| Colorectal cancer | 36 | Normal | Normal | 42 | Normal |
| Colorectal cancer | 36 | Normal | Normal | 41 | Normal |
| Colorectal cancer | 36 | Normal | Normal | 42 | Normal |
| Colorectal cancer | 35 | Normal | Normal | 41 | Normal |
| Colorectal cancer | 35 | Intestinal cancer | Normal | 40 | Normal |
| Colorectal cancer | 35 | Intestinal cancer | Normal | 40 | Normal |
| Colorectal cancer | 35 | Intestinal cancer | Normal | 40 | Normal |
| Colorectal cancer | 35 | Intestinal cancer | Normal | 40 | Normal |
| Colorectal cancer | 35 | Intestinal cancer | Normal | 40 | Normal |
| Colorectal cancer | 34 | Intestinal cancer | Normal | 40 | Normal |
| Colorectal cancer | 34 | Intestinal cancer | Normal | 39 | Normal |
| Colorectal cancer | 34 | Intestinal cancer | Normal | 39 | Normal |
| Colorectal cancer | 34 | Intestinal cancer | Normal | 39 | Normal |
| Colorectal cancer | 34 | Intestinal cancer | Normal | 39 | Normal |
| Colorectal cancer | 34 | Intestinal cancer | Normal | 39 | Normal |
| Colorectal cancer | 34 | Intestinal cancer | Normal | 39 | Normal |
| Colorectal cancer | 33 | Intestinal cancer | Normal | 39 | Normal |
| Colorectal cancer | 33 | Intestinal cancer | Normal | 39 | Normal |
| Colorectal cancer | 33 | Intestinal cancer | Normal | 39 | Normal |
| Colorectal cancer | 33 | Intestinal cancer | Normal | 39 | Normal |
| Colorectal cancer | 33 | Intestinal cancer | Normal | 39 | Normal |
| Colorectal cancer | 33 | Intestinal cancer | Normal | 39 | Normal |
| Colorectal cancer | 32 | Intestinal cancer | Normal | 39 | Normal |
| Colorectal cancer | 32 | Intestinal cancer | Normal | 39 | Normal |
| Colorectal cancer | 32 | Intestinal cancer | Normal | 39 | Normal |
| Colorectal cancer | 32 | Intestinal cancer | Normal | 38 | Normal |
| Colorectal cancer | 32 | Intestinal cancer | Normal | 38 | Normal |
| Colorectal cancer | 31 | Intestinal cancer | Normal | 39 | Normal |
| Colorectal cancer | 31 | Intestinal cancer | Normal | 38 | Normal |
| Colorectal cancer | 31 | Intestinal cancer | Normal | 38 | Normal |
| Colorectal cancer | 30 | Intestinal cancer | Normal | 38 | Normal |
| Colorectal cancer | 30 | Intestinal cancer | Normal | 38 | Normal |
| Colorectal cancer | 30 | Intestinal cancer | Normal | 38 | Normal |
| Colorectal cancer | 30 | Intestinal cancer | Normal | 38 | Normal |
| Colorectal cancer | 30 | Intestinal cancer | Normal | 38 | Normal |
| Colorectal cancer | 30 | Intestinal cancer | Normal | 38 | Normal |
| Colorectal cancer | 30 | Intestinal cancer | Normal | 38 | Normal |
| Colorectal cancer | 30 | Intestinal cancer | Normal | 38 | Normal |
| Colorectal cancer | 30 | Intestinal cancer | Normal | 38 | Normal |
| Colorectal cancer | 30 | Intestinal cancer | Normal | 38 | Normal |
| Colorectal cancer | 30 | Intestinal cancer | Normal | 37 | Normal |
| Colorectal cancer | 29 | Intestinal cancer | Normal | 38 | Normal |
| Colorectal cancer | 29 | Intestinal cancer | Normal | 37 | Normal |

TABLE 1-continued 163 cases of fecal specimens

| Classification of specimens | $C_T$ value | Detection and interpretation | Classification of specimens | $C_T$ value | Detection and interpretation |
|---|---|---|---|---|---|
| Colorectal cancer | 29 | Intestinal cancer | Normal | 38 | Normal |
| Colorectal cancer | 29 | Intestinal cancer | Normal | 37 | Normal |
| Colorectal cancer | 29 | Intestinal cancer | Normal | 38 | Normal |
| Colorectal cancer | 29 | Intestinal cancer | Normal | 37 | Normal |
| Colorectal cancer | 28 | Intestinal cancer | Normal | 38 | Normal |
| Colorectal cancer | 28 | Intestinal cancer | Normal | 37 | Normal |
| Colorectal cancer | 28 | Intestinal cancer | Normal | 37 | Normal |
| Colorectal cancer | 28 | Intestinal cancer | Normal | 37 | Normal |
| Colorectal cancer | 28 | Intestinal cancer | Normal | 37 | Normal |
| Colorectal cancer | 28 | Intestinal cancer | Normal | 37 | Normal |
| Colorectal cancer | 28 | Intestinal cancer | Normal | 37 | Normal |
| Colorectal cancer | 28 | Intestinal cancer | Normal | 37 | Normal |
| Colorectal cancer | 28 | Intestinal cancer | Normal | 37 | Normal |
| Colorectal cancer | 28 | Intestinal cancer | Normal | 37 | Normal |
| Colorectal cancer | 28 | Intestinal cancer | Normal | 37 | Normal |
| Colorectal cancer | 28 | Intestinal cancer | Normal | 37 | Normal |
| Colorectal cancer | 28 | Intestinal cancer | Normal | 36 | Normal |
| Colorectal cancer | 27 | Intestinal cancer | Normal | 37 | Normal |
| Colorectal cancer | 27 | Intestinal cancer | Normal | 37 | Normal |
| Colorectal cancer | 27 | Intestinal cancer | Normal | 36 | Normal |
| Colorectal cancer | 27 | Intestinal cancer | Normal | 36 | Normal |
| Colorectal cancer | 27 | Intestinal cancer | Normal | 36 | Normal |
| Colorectal cancer | 26 | Intestinal cancer | Normal | 36 | Normal |
| Colorectal cancer | 26 | Intestinal cancer | Normal | 36 | Normal |
| Colorectal cancer | 25 | Intestinal cancer | Normal | 36 | Normal |
| Colorectal cancer | 25 | Intestinal cancer | Normal | 35 | Normal |
| Colorectal cancer | 24 | Intestinal cancer | Normal | 35 | Intestinal cancer |
| | | | Normal | 35 | Intestinal cancer |
| | | | Normal | 35 | Intestinal cancer |
| | | | Normal | 35 | Intestinal cancer |

Note:
"non-amplification" means no amplification curve, no Ct data, and falls within a range greater than a threshold.

Example 2

105 pairs of colorectal cancer and normal para-carcinoma tissue specimens (confirmed by enteroscopy or pathology) were selected. According to the protocol, tissue DNA was extracted by QIAamp DNA Kit (QIAGEN), and then DNA was transformed by EZ DNA Methylation Kit (Zymo Research).

Then qMSP was performed to detect the methylation level of COL4A1.

qMSP Reaction System and Reaction Procedures were the same as the feces test in Example 1. And finally the methylation value of the gene in the specimens was calculated according to a standard curve: (Target/ACTB)*100. The qMSP primer and probe used was the same as in Example 1.

Figure 3:
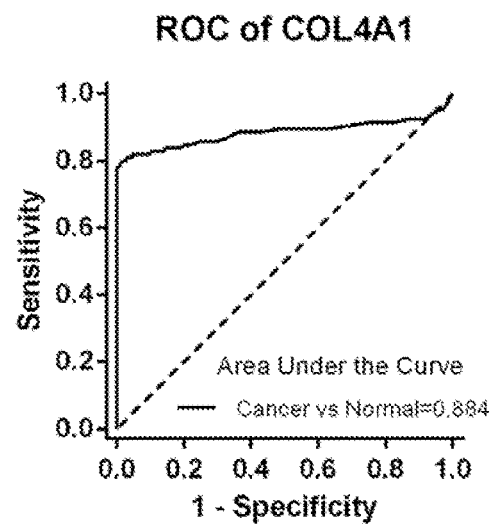
FIG. 3 shows a ROC curve of COL4A1 gene for colorectal cancer detection in the tissue test of Example 2.

In a tissue test, the ROC curve of COL4A1 gene for colorectal cancer detection is shown in FIG. 3:

For colorectal cancer, the detection sensitivity of COL4A1 gene is 81.9% (86/105), the specificity is 95.2% (100/105), and the area under ROC curve is 0.884 (95% CI: 0.829-0.939, p<0.001).

TABLE 2

105 pairs of cancer and normal para-carcinoma tissue

| Classification of specimens | Methylation value | Detection and interpretation | Classification of specimens | Methylation value | Detection and interpretation |
|---|---|---|---|---|---|
| Colorectal cancer | 0.0 | Normal | Normal | 0.0 | Normal |
| Colorectal cancer | 0.0 | Normal | Normal | 0.0 | Normal |
| Colorectal cancer | 0.0 | Normal | Normal | 0.0 | Normal |
| Colorectal cancer | 0.0 | Normal | Normal | 0.1 | Normal |
| Colorectal cancer | 0.0 | Normal | Normal | 0.2 | Normal |
| Colorectal cancer | 0.2 | Normal | Normal | 0.2 | Normal |
| Colorectal cancer | 0.3 | Normal | Normal | 0.3 | Normal |
| Colorectal cancer | 0.3 | Normal | Normal | 0.3 | Normal |
| Colorectal cancer | 0.5 | Normal | Normal | 0.3 | Normal |
| Colorectal cancer | 0.7 | Normal | Normal | 0.4 | Normal |
| Colorectal cancer | 0.8 | Normal | Normal | 0.4 | Normal |
| Colorectal cancer | 1.1 | Normal | Normal | 0.4 | Normal |
| Colorectal cancer | 1.3 | Normal | Normal | 0.4 | Normal |
| Colorectal cancer | 1.3 | Normal | Normal | 0.4 | Normal |
| Colorectal cancer | 1.4 | Normal | Normal | 0.5 | Normal |
| Colorectal cancer | 1.7 | Normal | Normal | 0.5 | Normal |

TABLE 2-continued

| 105 pairs of cancer and normal para-carcinoma tissue ||||||
|---|---|---|---|---|---|
| Classification of specimens | Methylation value | Detection and interpretation | Classification of specimens | Methylation value | Detection and interpretation |
| Colorectal cancer | 1.9 | Normal | Normal | 0.5 | Normal |
| Colorectal cancer | 2.2 | Normal | Normal | 0.5 | Normal |
| Colorectal cancer | 3.1 | Normal | Normal | 0.6 | Normal |
| Colorectal cancer | 3.9 | Intestinal cancer | Normal | 0.6 | Normal |
| Colorectal cancer | 4.8 | Intestinal cancer | Normal | 0.6 | Normal |
| Colorectal cancer | 5.1 | Intestinal cancer | Normal | 0.6 | Normal |
| Colorectal cancer | 5.5 | Intestinal cancer | Normal | 0.6 | Normal |
| Colorectal cancer | 6.5 | Intestinal cancer | Normal | 0.6 | Normal |
| Colorectal cancer | 7.0 | Intestinal cancer | Normal | 0.6 | Normal |
| Colorectal cancer | 8.2 | Intestinal cancer | Normal | 0.6 | Normal |
| Colorectal cancer | 8.5 | Intestinal cancer | Normal | 0.7 | Normal |
| Colorectal cancer | 9.1 | Intestinal cancer | Normal | 0.7 | Normal |
| Colorectal cancer | 9.3 | Intestinal cancer | Normal | 0.7 | Normal |
| Colorectal cancer | 10.8 | Intestinal cancer | Normal | 0.7 | Normal |
| Colorectal cancer | 10.8 | Intestinal cancer | Normal | 0.7 | Normal |
| Colorectal cancer | 11.3 | Intestinal cancer | Normal | 0.7 | Normal |
| Colorectal cancer | 11.3 | Intestinal cancer | Normal | 0.8 | Normal |
| Colorectal cancer | 12.7 | Intestinal cancer | Normal | 0.8 | Normal |
| Colorectal cancer | 12.9 | Intestinal cancer | Normal | 0.8 | Normal |
| Colorectal cancer | 13.6 | Intestinal cancer | Normal | 0.8 | Normal |
| Colorectal cancer | 13.9 | Intestinal cancer | Normal | 0.8 | Normal |
| Colorectal cancer | 14.2 | Intestinal cancer | Normal | 0.8 | Normal |
| Colorectal cancer | 14.3 | Intestinal cancer | Normal | 0.8 | Normal |
| Colorectal cancer | 14.8 | Intestinal cancer | Normal | 0.9 | Normal |
| Colorectal cancer | 15.7 | Intestinal cancer | Normal | 0.9 | Normal |
| Colorectal cancer | 17.0 | Intestinal cancer | Normal | 0.9 | Normal |
| Colorectal cancer | 17.6 | Intestinal cancer | Normal | 0.9 | Normal |
| Colorectal cancer | 17.9 | Intestinal cancer | Normal | 0.9 | Normal |
| Colorectal cancer | 18.7 | Intestinal cancer | Normal | 0.9 | Normal |
| Colorectal cancer | 19.3 | Intestinal cancer | Normal | 1.0 | Normal |
| Colorectal cancer | 19.4 | Intestinal cancer | Normal | 1.0 | Normal |
| Colorectal cancer | 19.6 | Intestinal cancer | Normal | 1.0 | Normal |
| Colorectal cancer | 20.1 | Intestinal cancer | Normal | 1.0 | Normal |
| Colorectal cancer | 20.2 | Intestinal cancer | Normal | 1.0 | Normal |
| Colorectal cancer | 20.9 | Intestinal cancer | Normal | 1.0 | Normal |
| Colorectal cancer | 21.2 | Intestinal cancer | Normal | 1.0 | Normal |
| Colorectal cancer | 21.3 | Intestinal cancer | Normal | 1.0 | Normal |
| Colorectal cancer | 21.6 | Intestinal cancer | Normal | 1.0 | Normal |
| Colorectal cancer | 21.8 | Intestinal cancer | Normal | 1.1 | Normal |
| Colorectal cancer | 21.8 | Intestinal cancer | Normal | 1 1 | Normal |
| Colorectal cancer | 21.8 | Intestinal cancer | Normal | 1.1 | Normal |
| Colorectal cancer | 22.0 | Intestinal cancer | Normal | 1.1 | Normal |
| Colorectal cancer | 23.0 | Intestinal cancer | Normal | 1.1 | Normal |
| Colorectal cancer | 23.4 | Intestinal cancer | Normal | 1.1 | Normal |
| Colorectal cancer | 23.5 | Intestinal cancer | Normal | 1.2 | Normal |
| Colorectal cancer | 24.2 | Intestinal cancer | Normal | 1.2 | Normal |
| Colorectal cancer | 25.3 | Intestinal cancer | Normal | 1.2 | Normal |
| Colorectal cancer | 25.8 | Intestinal cancer | Normal | 1.2 | Normal |
| Colorectal cancer | 25.9 | Intestinal cancer | Normal | 1.2 | Normal |
| Colorectal cancer | 26.8 | Intestinal cancer | Normal | 1.2 | Normal |
| Colorectal cancer | 27.2 | Intestinal cancer | Normal | 1.2 | Normal |
| Colorectal cancer | 27.4 | Intestinal cancer | Normal | 1.3 | Normal |
| Colorectal cancer | 28.1 | Intestinal cancer | Normal | 1.3 | Normal |
| Colorectal cancer | 28.2 | Intestinal cancer | Normal | 1.3 | Normal |
| Colorectal cancer | 28.7 | Intestinal cancer | Normal | 1.3 | Normal |
| Colorectal cancer | 29.7 | Intestinal cancer | Normal | 1.4 | Normal |
| Colorectal cancer | 30.3 | Intestinal cancer | Normal | 1.4 | Normal |
| Colorectal cancer | 31.4 | Intestinal cancer | Normal | 1.4 | Normal |
| Colorectal cancer | 31.9 | Intestinal cancer | Normal | 1.5 | Normal |
| Colorectal cancer | 32.0 | Intestinal cancer | Normal | 1.5 | Normal |
| Colorectal cancer | 32.3 | Intestinal cancer | Normal | 1.5 | Normal |
| Colorectal cancer | 35.4 | Intestinal cancer | Normal | 1.6 | Normal |
| Colorectal cancer | 36.1 | Intestinal cancer | Normal | 1.6 | Normal |
| Colorectal cancer | 36.3 | Intestinal cancer | Normal | 1.7 | Normal |
| Colorectal cancer | 36.7 | Intestinal cancer | Normal | 1.7 | Normal |
| Colorectal cancer | 37.1 | Intestinal cancer | Normal | 1.7 | Normal |
| Colorectal cancer | 39.1 | Intestinal cancer | Normal | 1.8 | Normal |
| Colorectal cancer | 39.3 | Intestinal cancer | Normal | 1.8 | Normal |
| Colorectal cancer | 40.4 | Intestinal cancer | Normal | 1.9 | Normal |
| Colorectal cancer | 40.8 | Intestinal cancer | Normal | 2.0 | Normal |
| Colorectal cancer | 41.8 | Intestinal cancer | Normal | 2.0 | Normal |
| Colorectal cancer | 41.9 | Intestinal cancer | Normal | 2.1 | Normal |
| Colorectal cancer | 42.4 | Intestinal cancer | Normal | 2.1 | Normal |
| Colorectal cancer | 45.9 | Intestinal cancer | Normal | 2.1 | Normal |
| Colorectal cancer | 50.1 | Intestinal cancer | Normal | 2.5 | Normal |

TABLE 2-continued 105 pairs of cancer and normal para-carcinoma tissue

| Classification of specimens | Methylation value | Detection and interpretation | Classification of specimens | Methylation value | Detection and interpretation |
|---|---|---|---|---|---|
| Colorectal cancer | 52.0 | Intestinal cancer | Normal | 2.6 | Normal |
| Colorectal cancer | 55.3 | Intestinal cancer | Normal | 2.7 | Normal |
| Colorectal cancer | 56.3 | Intestinal cancer | Normal | 2.8 | Normal |
| Colorectal cancer | 56.6 | Intestinal cancer | Normal | 3.1 | Normal |
| Colorectal cancer | 56.8 | Intestinal cancer | Normal | 3.2 | Normal |
| Colorectal cancer | 58.6 | Intestinal cancer | Normal | 3.2 | Normal |
| Colorectal cancer | 65.0 | Intestinal cancer | Normal | 3.6 | Normal |
| Colorectal cancer | 66.9 | Intestinal cancer | Normal | 3.7 | Normal |
| Colorectal cancer | 69.1 | Intestinal cancer | Normal | 3.8 | Normal |
| Colorectal cancer | 70.8 | Intestinal cancer | Normal | 4.0 | Intestinal cancer |
| Colorectal cancer | 73.4 | Intestinal cancer | Normal | 4.5 | Intestinal cancer |
| Colorectal cancer | 84.7 | Intestinal cancer | Normal | 4.9 | Intestinal cancer |
| Colorectal cancer | 92.8 | Intestinal cancer | Normal | 5.1 | Intestinal cancer |
| Colorectal cancer | 99.8 | Intestinal cancer | Normal | 5.6 | Intestinal cancer |

Comparative Example 1

Currently, in some studies, DNA from fecal specimens was extracted using QIAamp DNA Feces Mini Kit (QIA-GEN), and then a qualitative or quantitative detection of the level of markers in the specimens was performed using methylation-specific PCR (MSP) or quantitative methylation-specific PCR (qMSP). Wherein, electrophoresis is required for the detection of colorectal cancer by MSP, so that it is more inconvenient to operate and there is a risk of products contamination; the DNA in the feces extracted by the QIAamp DNA Feces Mini Kit is the total DNA of human and bacteria, with few DNA of real human tumor, which is not conducive to subsequent PCR detection.

Comparative Example 2

Studies have shown that SFRP1 gene methylation is associated with intestinal cancer, and colorectal cancer can be detected by detecting the methylation level of this gene in feces. In the test of 53 cases of fecal specimens (29 cases of intestinal cancer, 7 cases of adenoma, 17 cases of normal), 89% colorectal tumors were detected with a specificity of 86%. (Zhang W, Bauer M, Croner R S, Pelz J O, Lodygin D, Hermeking H, Sturzl M, Hohenberger W, Matzel K E. DNA feces test for colorectal cancer: Hypermethylation of the secreted frizzled-related protein-1 gene. DISEASES OF THE COLON & RECTUM 2007; 50(10): 1618-26; discussion 1626-7.)

Figure 4:
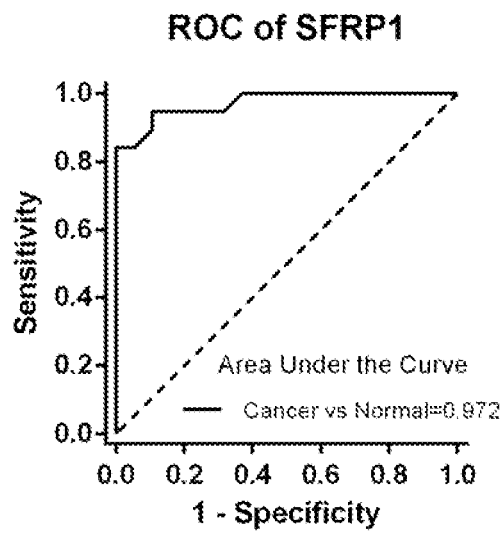
FIG. 4 shows a ROC curve of SFRP1 gene for colorectal cancer detection in 19 pairs of tissue test of Comparative Example 2.

The methylation level of the SFRP1 gene was also detected in 19 pairs of tissues and 36 cases of fecal specimens, and the extraction method for target gene was the same as in Examples 1 and 2. In the test of 19 pairs of tissues, the ROC curve of SFRP1 gene for colorectal cancer detection is shown in FIG. 4:

For colorectal cancer tissues, the detection sensitivity of SFRP1 gene is 89%, the specificity is 95%, and the area under ROC curve is 0.972 (95% CI: 0.929-1, $p<0.001$).

Figure 5:
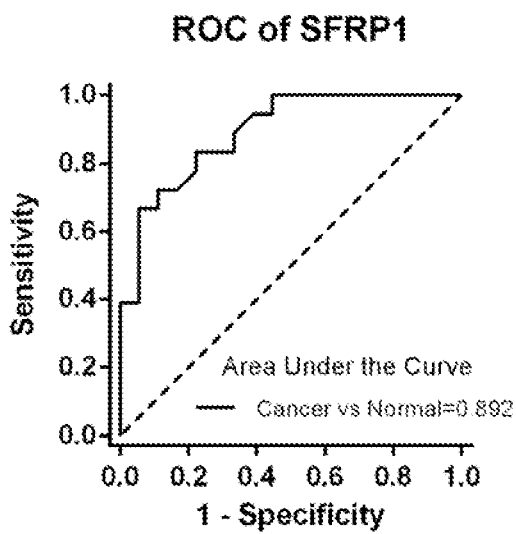
FIG. 5 shows a ROC curve of SFRP1 gene for colorectal cancer detection in 36 feces test of Comparative Example 2.

In the test of 36 cases of fecal specimens, the ROC curve of SFRP1 gene for colorectal cancer detection is shown in FIG. 5:

For colorectal cancer, the detection sensitivity of SFRP1 gene is 67%, the specificity is 94%, and the area under ROC curve is 0.892 (95% CI: 0.790-0.994, $p<0.0001$).

Therefore, the SFRP1 gene has high detection sensitivity and specificity on colorectal cancer tissues, however the sensitivity of the SFRP1 gene in fecal specimens is greatly reduced.

The foregoing is only a preferred embodiment of the present invention, and it should be noted that, for those skilled in the art, various modifications and amendments can be made without departing from the principle of the present invention, and these modifications and amendments should also be considered as the protection scope of the present invention.

What is claimed is:

1. A methylation detection kit of COL4A1 gene, comprising:
   a gene capturing reagent comprising a magnetic bead probe complex;
   a capture sequence having a nucleotide sequence having at least 85% identity to SEQ ID NO: 1;
   a first primer having a nucleotide sequence having at least 85% identity to SEQ ID NO: 2;
   a second primer having a nucleotide sequence having at least 85% identity to SEQ ID NO: 3; and
   a probe having a nucleotide sequence having at least 85% identity to SEQ ID NO: 4.

2. The kit of claim 1, wherein said capture sequence has a nucleotide sequence having at least 90% identity to SEQ ID NO: 1.

3. The kit of claim 1, wherein said first primer has a nucleotide sequence having at least 90% identity to SEQ ID NO: 2.

4. The kit of claim 1, wherein said second primer has a nucleotide sequence having at least 90% identity to SEQ ID NO: 3.

5. The kit of claim 1, wherein said probe has a nucleotide sequence having at least 90% identity to SEQ ID NO: 4.

6. The kit of claim 1, wherein said capture sequence has a nucleotide sequence having at least 95% identity to SEQ ID NO: 1.

7. The kit of claim 1, wherein said first primer has a nucleotide sequence having at least 95% identity to SEQ ID NO: 2.

8. The kit of claim 1, wherein said second primer has a nucleotide sequence having at least 95% identity to SEQ ID NO: 3.

9. The kit of claim 1, wherein said probe has a nucleotide sequence having at least 95% identity to SEQ ID NO: 4.

10. The kit of claim 1, wherein said capture sequence has a nucleotide sequence comprises SEQ ID NO: 1.

11. The kit of claim 1, wherein said first primer has a nucleotide sequence comprises SEQ ID NO: 2.

12. The kit of claim 1, wherein said second primer has a nucleotide sequence comprises SEQ ID NO: 3.

13. The kit of claim 1, wherein said probe has a nucleotide sequence comprises SEQ ID NO: 4.

14. A method for detecting a colorectal carcinoma or colorectal adenoma in a human subject, comprising:
   obtaining an excrement sample from the human subject;
   extracting DNA from said excrement sample;
   converting the extracted DNA;
   amplifying the converted DNA and obtaining a COL4A1 methylation level of an amplification product; and
   detecting the presence of the colorectal carcinoma or colorectal adenoma in the human subject when the COL4A1 methylation level of the amplification product is greater in comparison to a COL4A1 methylation level of an amplification product in a control excrement sample from human subjects that do not have said colorectal carcinoma or colorectal adenoma,
   wherein said amplifying the converted DNA and obtaining the COL4A1 methylation level of the amplification product comprises:
   using the kit of claim 1.

* * * * *

SEQUENCE LISTING

```
<160> NUMBER OF SEQ ID NOS: 4

<210> SEQ ID NO 1
<211> LENGTH: 40
<212> TYPE: DNA
<213> ORGANISM: Artificial Sequence
<220> FEATURE:
<223> OTHER INFORMATION: Synthetic sequence, COL4A1 capture sequence

<400> SEQUENCE: 1
ctgcccggcg tgcgggggcc gcggcggaca gctagctctc                          40

<210> SEQ ID NO 2
<211> LENGTH: 20
<212> TYPE: DNA
<213> ORGANISM: Artificial Sequence
```

```
<220> FEATURE:
<223> OTHER INFORMATION: Synthetic oligonucleotide primer

<400> SEQUENCE: 2
cgtttggagt cgtcgtattc                                          20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 3
cgacgaacaa ctaactctcg                                          20

<210> SEQ ID NO 4
<211> LENGTH: 24
<212> TYPE: DNA
<213> ORGANISM: Artificial Sequence
<220> FEATURE:
<223> OTHER INFORMATION: Synthetic probe sequence

<400> SEQUENCE: 4
cgtagcgttg gaagttcggt tttt                                     24
```